United States Patent [19]

Eaton et al.

[11] Patent Number: 4,674,110
[45] Date of Patent: Jun. 16, 1987

[54] HAND AND FINGER X-RAY POSITIONING DEVICE

[76] Inventors: Richard G. Eaton, 640 Ely Ave., Pelham Manor, N.Y. 10803; John J. Keyser, 2 Crest Acre Ct., Summit, N.J. 07901

[21] Appl. No.: 681,689

[22] Filed: Dec. 14, 1984

[51] Int. Cl.⁴ .............................................. H05G 1/00
[52] U.S. Cl. .................................. 378/208; 378/180; 128/77
[58] Field of Search ................... 378/208, 180; 128/77

[56] References Cited

U.S. PATENT DOCUMENTS

| 3,526,222 | 9/1970 | Dreibelbis | 378/208 |
| 3,639,764 | 2/1972 | Olson et al. | 378/180 |
| 4,316,454 | 2/1982 | Perka | 128/77 |

Primary Examiner—Craig E. Church
Assistant Examiner—David Porta
Attorney, Agent, or Firm—Kenyon & Kenyon

[57] ABSTRACT

A hand and finger X-ray positioning device comprising a radiolucent support board containing one or more attachment means and one or more positioning means which are removably affixed to said attachment means and which permit the stable positioning of one or more fingers in a desired position for the purpose of obtaining X-rays of the hand and fingers without exposing a surgeon or technician to harmful radiation. In a preferred embodiment, the attachment means are a series of holes located at the distal end of a sterilizable rectangular support board into which fit the positioning means or pegs.

9 Claims, 4 Drawing Figures

U.S. Patent  Jun. 16, 1987  4,674,110
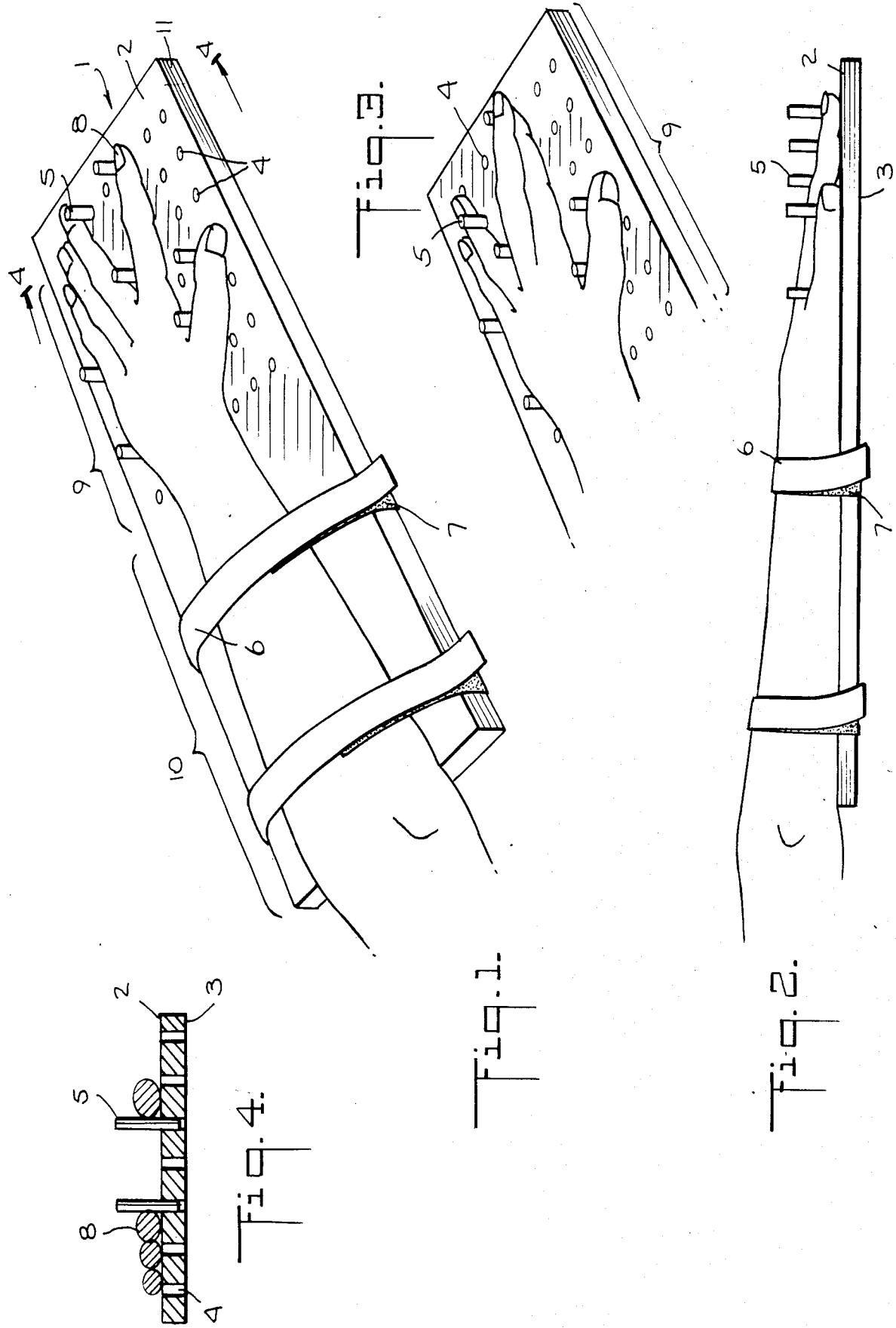

HAND AND FINGER X-RAY POSITIONING DEVICE

FIELD OF THE INVENTION

This invention relates generally to the field of surgery and more particularly to a device used for the stable and flexible positioning of the fingers and hand for the safe procurement of X-rays thereof.

BACKGROUND OF THE INVENTION

The anatomy of the fingers and hand is such that surgery on those areas can present the surgeon with vexating problems relating not only to the particular medical problem involved, but also to the location of and the proper access to the area of concern in order to conveniently perform required surgery. Proper positioning of the fingers and hand during the taking of X-rays of those portions of the anatomy undergoing surgery facilitates and simplifies what is often a delicate and complicated surgical procedure, especially when considered in light of the complexity of the bone structure, vascular network and nervous system components present in the hand and fingers. In order to position the hand and fingers for the purpose of taking X-rays, particularly in connection with the performance of surgery, it has heretofore been necessary for the surgeon or a technician to manually hold the hand and fingers in place which often proved inadequate in achieving the desired position of the hand and fingers. Moreover, and perhaps more importantly, the surgeon or technician is exposed to the dangerous radiation emitted by the X-rays. Lead aprons scarcely allay the fear of the surgeon or technician, who is exposed time and time again to this dangerous radiation.

Prior devices for positioning the hand and/or arm have generally not been designed for the purpose of stably positioning the fingers and hand during the taking of X-rays and therefore are inadequate to solve the many problems faced by the surgeon or technician seeking to obtain proper positioning for the purpose of obtaining X-rays. For instance, U.S. Pat. No. 4,316,454 to Perka is a therapeutic positioning device for a paralyzed limb having either a flaccid or spastic condition and consists of a support board and a rod capable of being positioned in any one of a plurality of holes, the rod being of a size which permits a hand to be placed directly next to, and if possible, in a holding position around the rod. U.S. Pat. No. 1,879,401 to Monaco discloses an exercising device for paralyzed limbs in which pegs are used for the purpose of exercising the paralyzed limb, U.S. Pat. No. 3,903,878 to Spann discloses a device for supporting a hand or foot to prevent making use of a polyurethane block, U.S. Pat. No. 3,480,013 to Garber discloses a limb restraint device for intravenous injections and the like, and U.S. Pat. No. 3,568,671 to Graham discloses a splint formed of three tapered segments joined end-to-end.

An attempt to simplify and provide a more stable positioning of the forearm, hand and fingers during surgery is evident in U.S. Pat. No. 3,746,332 to Hakstian which provides for a workbench formed of a ramp for the positioning of a patient's forearm, the ramp merging into a horizontal platform for the placing of the patient's wrist and hand. Other attempts to solve positioning problems during surgery are disclosed in U.S. Pat. No. 4,204,533 to Forster et al. (A surgical element for fixing the position of the hand and fingers during an operation utilizing movable rings to secure the fingers of the patient during surgery) and U.S. Pat. No. 4,082,257 to Strickland (surgery table which utilizes straps and a finger loop retractor to secure portions of the hand during surgery). None of these patents, however, has addressed the problems associated with the proper positioning of the hand and fingers for the purpose of safely procuring X-rays, particularly before, during and after surgery. Any device used for this purpose in the prior art would not allow the proper flexibility in positioning the hand and fingers and in any event would not be conducive to the taking of X-rays since they are of a radiopaque nature.

Thus, there remains a need for a device that will permit a great degree of flexibility in the stable positioning of the hand and fingers for a purpose of taking X-rays while eliminating the need for the surgeon or technician to be exposed to harmful radiation.

SUMMARY OF THE INVENTION

It is an object of this invention to provide a hand and finger X-ray positioning device which has means for stably positioning the hand and fingers in a desired manner for the purpose of obtaining X-rays and which conveniently facilitates the changing of the positioning thereof before, during and after the performance of a surgical procedure.

It is also an object of this invention to provide an improved hand and finger X-ray positioning device which permits the use of X-rays while the hand and fingers are stably positioned before, during and after the performance of a surgical procedure, without exposing a surgeon or technician to the harmful effects of X-ray radiation.

These and other objects are achieved through the provision of a hand and finger X-ray positioning device for use in obtaining X-rays of the hand and fingers. In the preferred embodiment, the device provides a support board containing a series of holes at the distal end thereof suitable for the placement of one or more pegs therein which ensures the stable and flexible positioning of the hand and fingers once the arm has been securely fastened to the support board. The support board is made up of radiolucent material which permits the taking of X-rays of the hand and fingers. Preferably, the device is sterilizable so as to permit repeated use.

BRIEF DESCRIPTION OF THE DRAWINGS

FIG. 1 is a perspective view of one embodiment of the invention.

FIG. 2 is a side view of the device shown in FIG. 1.

FIG. 3 is a perspective view of the distal end of the device illustrating a manner in which the hand and fingers may be situated.

FIG. 4 is a cross-sectional view of FIG. 1 at the tips of the fingers.

DESCRIPTION OF PREFERRED EMBODIMENTS

Referring to the drawings, the support board 1 of the inventive device has a substantially rectangular shape formed by a top planar surface 2 and a bottom planar surface 3, and is made up of the forearm region 10 and the distal region 9. The bottom planar surface 3 permits the support board 1 to be placed on virtually any base suitable for the taking of X-rays. The width 11 of the support board 1, or that segment exisiting between the top planar surface 2 and the bottom planar surface 3, can be of any size provided that the forearm and hand can be stably positioned thereon and the bottom planar surface can securely rest on a surface that permits the taking of X-rays. Preferably, the rectangular support board measures about 7 inches by about 24 inches.

The distal region 9 of the support board 1 contains a series of attachment means or holes 4 which are desirably arranged to lie under the entire hand from the top of the fingers to the base of the thumb or wrist region of the arm. Preferably, the holes 4 are arranged in rows as depicted in FIGS. 1 and 3 close enough together so as to afford a maximum degree of flexibility to the surgeon or X-ray technician in arranging the position of the hand and fingers utilizing the positioning means or pegs 5.

The holes 4 should be of such a size and character that will firmly hold the positioning means or pegs 5 but yet allow for their convenient removal. Ideally, the holes 4 are spaced sufficiently apart so as to permit the pegs to be placed in any given arrangement without interference from other pegs.

The straps 6 act to securely fasten the arm of the patient. Any type or number of straps 6 are appropriate for use with the invention, but the preferred strap calls for the use of a "velcro" fastener 7 which facilitates the fastening and unfastening of the arm. This, of course, would aid the surgeon or technician in obtaining the proper placement of the hand and fingers, as well as provide for the quick and easy fastening and unfastening of the patient's arm.

The support board itself may be of any width and shape provided the hand and fingers may be arranged thereon so as to permit the desired positioning thereof for the taking of X-rays. So as to avoid movement of the arm, the forearm should be fastened in some manner. In the preferred embodiment, the support board is a rectangularly shaped structure with a series of holes for the placement of one or more pegs at the distal end thereof with one or more velcro fasteners across the forearm region for the purpose of securing the forearm in place. In this preferred embodiment, the rectangular support board extends approximately from the elbow to the tips of the fingers of a patient. The support board, however, does not have to be of rectangular configuration in order to practice the invention, nor does the attachment means or holes have to be located at the distal end thereof.

The support board is composed of a radiolucent material thereby permitting the taking of X-rays while the fingers and hand are desirably positioned using the pegs and holes. Any radiolucent material is adequate for this purpose, provided that it is strong enough to stably support the fingers, hand and arms and is capable of containing the attachment means or holes which will securely hold the removable positioning means or pegs. Exemplary radiolucent materials include substances such as plexiglass and lucite.

Since the support board may be used in connection with a surgical procedure and in any event is utilized in a health care environment, it should be capable of being autoclaved or exposed to some other sterilization device or procedure without an adverse effect to its structural integrity or to its radiolucent nature. In the alternative, the support board may be disposable provided that such disposable support board is structurally sound for the intended use of the board and is composed of a radiolument material.

At the distal end of the support board there exists some form of attachment means into which are inserted the positioning means which permits a multitude of finger and hand positions. In a preferred embodiment, the attachment means are holes which are arranged in a series of rows with each hole being equidistant from another. In a most preferred embodiment, the holes are spaced approximately one inch from each of its neighboring holes. In general, the greater the quantity of holes, the greater the flexibility that exists in achieving a variety of positions of the hand and fingers.

In the preferred embodiment, the positioning means are pegs which are suitably arranged in the holes in a way that permits the arranging of the hand and fingers in a desirable position while permitting the taking of X-rays. In this regard, the pegs are desirably composed of radiolucent material in addition to the support board.

Each peg is of sufficient height such that when inserted into a hole, it extends to the height needed to stably position one or more fingers arranged one on top of another. In this regard, the pegs may be of varying lengths and shapes so as to accommodate the variety of ways in which fingers may be arranged. Thus, the pegs may be all of one length or may vary in length, and in a preferred embodiment, may be from about one half inch to about three and one half inches.

In order to more securely position the hand and fingers, it is desirable to fasten the forearm region of the patient's arm to the support board with some form of strap or fastener. Such straps should be evenly spaced from the wrist area to the elbow area of the support board so as to ensure maximum containment of the arm and prevent the movement thereof which may alter the positioning of the hand and fingers achieved through the desired positioning of the positioning means or pegs.

Even though the device of the invention has been discussed herein in relation to human beings, the invention finds application in the veterinary field as well. For this reason, the words "hands" and "fingers", as used herein, refers to the human hand and fingers as well as the biological equivalent thereof in the animal kingdom, such as a "paw".

While there have been described what are presently believed to be preferred embodiments of the invention, it will be apparent to one skilled in the art that numerous changes can be made to the sizes and shapes set forth in the foregoing embodiments without departing from the invention as described herein and as defined in the appended claims.

What is claimed is:

1. A hand and finger X-ray positioning device comprising:
    (a) a radiolucent support board having a plurality of attachment means for securing an arm to said board which is suitable for taking an X-ray of the hand and fingers when placed thereon;
    (b) a plurality of positioning pegs for positioning individual fingers which are removably affixed to said attachment means and which permit the stable positioning of the hand and one or more fingers in a desired position for the purpose of obtaining X-rays of at least one of the hand and one or more fingers; and
    (c) wherein said positioning pegs are substantially perpendicular to said support board.

2. The hand and finger X-ray positioning device according to claim 1 wherein, the pegs are round pegs, the attachment means are holes into which a pegs may be removably affixed and the pegs are located at a distal end of the radiolucent support board.

3. The hand and finger X-ray positioning device according to claim 2 wherein the pegs are about one half inch to about three and one half inches in height.

4. The hand and finger X-ray positioning device according to claim 2 wherein the holes are arragned in a series of rows and are equidistant from one another.

5. A hand and finger X-ray positioning device comprising:
 (a) a radiolucent support board having a plurality of holes in a distal end portion thereof, said support board being suitable for taking an X-ray of the hand and fingers when placed thereon;
 (b) a plurality of pegs removably affixed in said holes far stably positioning the hand and one or more fingers in a desired position for the purpose of obtaining X-rays of at least one of the hand and one or more fingers; and
 (c) wherein said pegs are substantially perpendicular to said support board.

6. The hand and finger X-ray positioning device according to claim 5 wherein said support board is rectangular in shape such that the fingers of the hand lie over the distal end thereof.

7. The hand and finger X-ray positioning device according to claim 5 wherein the pegs are about one half inch to about three and one half inches in height.

8. The hand and finger X-ray positioning device according to claim 5 wherein the holes are arranged in a series of rows and are equidistant from one another.

9. A hand and finger X-ray positioning device comprising:
 (a) a radiolucent support board having a plurality of holes arranged in a series of rows approximately equidistant from one another in a distal end portion thereof suitable for the taking of X-rays of the hand and fingers when placed thereon;
 (b) a plurality of pegs of about one half inch to about three and one half inches removably affixed in said holes at right angles to the support board for stably positioning the hand and one or more fingers in a desired position for the purpose of obtaining X-rays of at least one of the hand and one or more fingers, said pegs being of sufficient height such that when inseted into the holes, they extend to a height needed to stably position one or more fingers arranged one on top of another.

* * * * *